United States Patent
Peyton et al.

(10) Patent No.: US 8,124,113 B2
(45) Date of Patent: Feb. 28, 2012

(54) HYDROPHILIC COATING

(75) Inventors: Barbara M. Peyton, Windsor, CT (US); John W. Steele, Hartford, CT (US)

(73) Assignee: Hamilton Sundstrand Space Systems International, Inc., Windsor Locks, CT (US)

( * ) Notice: Subject to any disclaimer, the term of this patent is extended or adjusted under 35 U.S.C. 154(b) by 1924 days.

(21) Appl. No.: 11/220,159

(22) Filed: Sep. 6, 2005

(65) Prior Publication Data

US 2007/0053946 A1    Mar. 8, 2007

(51) Int. Cl.
  *B05D 1/00* (2006.01)
  *C09D 5/14* (2006.01)
(52) U.S. Cl. .............. 424/405; 106/15.05; 106/14.5
(58) Field of Classification Search .......... 106/14.5; 424/405
  See application file for complete search history.

(56) References Cited

U.S. PATENT DOCUMENTS

| | | | |
|---|---|---|---|
| 3,658,581 A | 4/1972 | Paul | |
| 3,868,830 A | 3/1975 | Fletcher | |
| 5,264,250 A | 11/1993 | Steele | |
| 5,305,827 A | 4/1994 | Steele | |
| 5,562,949 A | 10/1996 | Steele | |
| 2004/0109853 A1* | 6/2004 | McDaniel | 424/94.6 |
| 2006/0086281 A1* | 4/2006 | Poulet et al. | 106/14.5 |

FOREIGN PATENT DOCUMENTS

WO    WO03/078683    *    9/2003

* cited by examiner

*Primary Examiner* — Frederick Krass
*Assistant Examiner* — Darryl C Sutton
(74) *Attorney, Agent, or Firm* — Carlson Gaskey & Olds, P.C.

(57) ABSTRACT

An antimicrobial coating slurry includes about 15.5 wt % of a wetting agent, about 6.0 wt % of an insolubilizer, about 1.1 wt % of a biocide agent, and about 7.8 wt % of an inorganic material that includes lithium oxide and the balance water. The slurry is applied to a heat exchanger surface, cured, and washed to form a hydrophilic coating that includes lithium silicate. The hydrophilic coating provides improved moisture wicking and a reduced dissolution rate of biocide, which is held within a lithium silicate matrix.

11 Claims, 2 Drawing Sheets

HYDROPHILIC COATING

BACKGROUND OF THE INVENTION

The present invention relates to hydrophilic coatings and, more particularly, to a hydrophilic coating composition for enhanced biocide dissolution.

Heat exchangers are widely known and used in, for example, space stations, space vehicles, and terrestrial cooling systems. Conventional heat exchangers include slurper bars coated with an antimicrobial hydrophilic coating that inhibits growth of micro-organisms and promotes condensation of condensed water from passing air. A vacuum source evacuates a passage in the slurper bars to collect the condensed water and prevent formation of water droplets that may otherwise reduce airflow. The condensed water is collected downstream, purified, and reused.

Conventional antimicrobial hydrophilic coatings are typically applied as a slurry to the slurper bars and cured at elevated temperatures. Upon curing, the slurry forms the antimicrobial hydrophilic coating, which wicks away condensed moisture on the slurper bars. Typical antimicrobial hydrophilic coatings include a matrix of potassium silicate and/or borosilicate in which a biocide resides, typically silver oxide. Disadvantageously, potassium silicate and/or borosilicate matrices are prone to cracking, flaking, and dissolution of the biocide into the condensed water. The condensed water and dissolved biocide collect downstream, where the zinc oxide often precipitates out of solution and forms a build-up on purifiers, filters, or other components. The build-up may inhibit proper operation of the cooling system.

Accordingly, an antimicrobial hydrophilic coating composition that is less prone to cracking, flaking, and biocide dissolution is needed.

SUMMARY OF THE INVENTION

The antimicrobial hydrophilic coating slurry composition according to the present invention includes about 15.5 wt % of a wetting agent, about 6.0 wt % of an insolubilizer, about 1.1 wt % of a biocide agent, about 7.8 wt % inorganics including lithium oxide, and the balance water. The slurry is applied to a surface of a heat exchanger slurper bar and cured at an elevated temperature to form an antimicrobial hydrophilic coating. The antimicrobial hydrophilic coating provides enhanced moisture wicking and a reduced dissolution rate of a biocide agent within the antimicrobial hydrophilic coating.

An example method for forming an antimicrobial hydrophilic coating includes curing the slurry at a temperature of about 500° F. for about four hours. The cured antimicrobial hydrophilic coating is then washed in water to remove unreacted components. The effluent wash water pH is monitored to determine the degree of washing.

BRIEF DESCRIPTION OF THE DRAWINGS

The various features and advantages of this invention will become apparent to those skilled in the art from the following detailed description of the currently preferred embodiment. The drawings that accompany the detailed description can be briefly described as follows.

DETAILED DESCRIPTION OF THE PREFERRED EMBODIMENT

Figure 1:
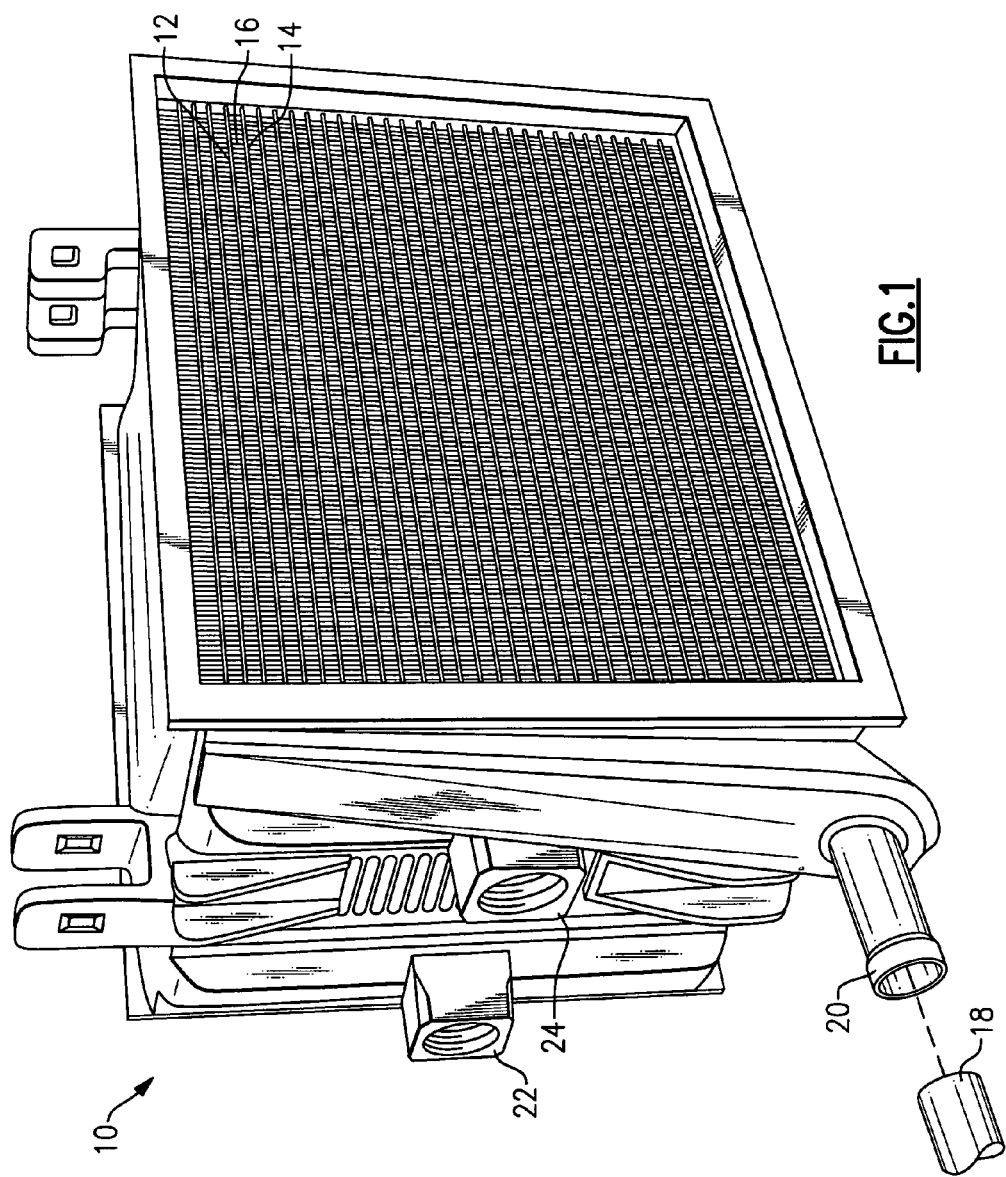
FIG. 1 is a schematic view of an example heat exchanger according to the present invention.

FIG. 1 illustrates selected portions of an example heat exchanger 10. In this example, the heat exchanger 10 includes slurper bars 12 in alternating configuration with cooling tubes 14. Fins 16 separate the slurper bars 12 and cooling tubes 14. The slurper bars 12 collect moisture from passing air and wick the moisture away from an air flow stream through the heat exchanger 10 to prevent condensation and formation of water droplets. The slurper bars 12 are in fluid communication with a vacuum source 18 that is connected to the heat exchanger 10 through a vacuum port 20 in a known manner. Coolant for cooling heat-producing units within a space station or space vehicle, for example, flows through the heat exchanger 10 through respective inlet and outlet ports 22 and 24.

Figure 2:
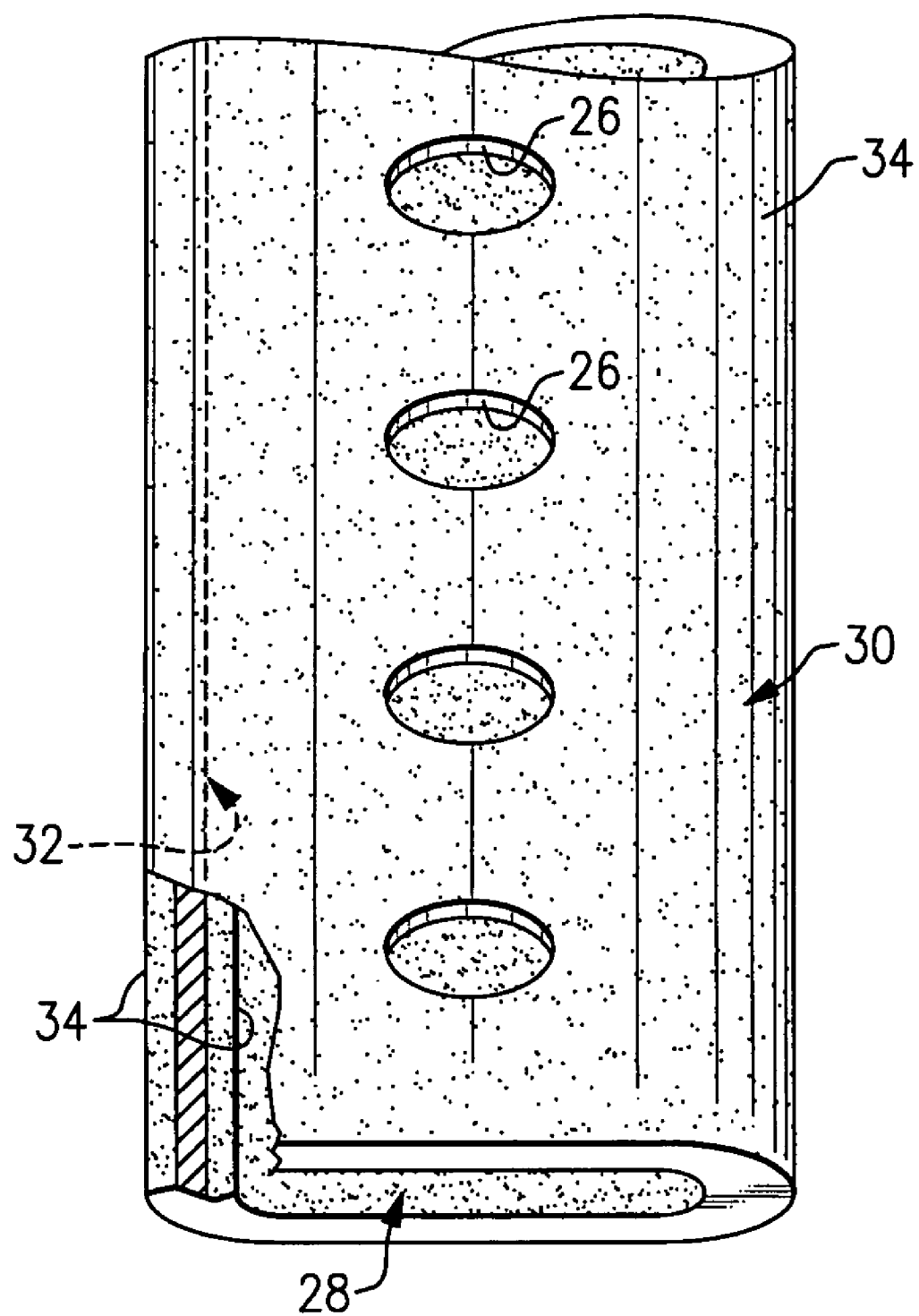
FIG. 2 is a schematic view of an example slurper bar.

Referring to FIG. 2, the slurper bars 12 each include openings 26 that fluidly connect a passage 28 to the passing air flow stream. The vacuum source 18 (FIG. 1) evacuates the passage 28. An outside surface 30 and an inner surface 32 of the passage are coated with a hydrophilic coating 34 that promotes moisture condensation and wicking. The hydrophilic coating 34 is prepared in a slurry and applied to the slurper bars 12 before a curing process.

In one example, the slurry includes a composition shown below:

| Component | Composition (wt %) |
|---|---|
| Wetting Agent - Silica Flour ($SiO_2$) | 13.9-17.1 |
| Insolubilizer - Zinc Oxide (ZnO) | 5.4-6.6 |
| Biocide - Silver Oxide (AgO) | 1.0-1.2 |
| Inorganic - Potassium Oxide ($K_2O$) | 0.9-1.1 |
| Inorganic - Lithium Oxide ($Li_2O$) | 0.2-0.8 |
| Inorganic - Silica (SiO2) | 5.7-6.9 |
| Water | balance |

In another example, the slurry includes the composition shown below:

| Component | Composition (wt %) |
|---|---|
| Wetting Agent - Silica Flour ($SiO_2$) | 15.2-15.8 |
| Insolubilizer - Zinc Oxide (ZnO) | 5.9-6.1 |
| Biocide - Silver Oxide (AgO) | 1.1 |
| Inorganic - Potassium Oxide ($K_2O$) | 1.0 |
| Inorganic - Lithium Oxide ($Li_2O$) | 0.5 |
| Inorganic - Silica (SiO2) | 6.2-6.4 |
| Water | balance |

In another example, the slurry includes the composition shown below:

| Component | Composition (wt %) |
|---|---|
| Wetting Agent - Silica Flour ($SiO_2$) | 15.5 |
| Insolubilizer - Zinc Oxide (ZnO) | 6.0 |
| Biocide - Silver Oxide (AgO) | 1.1 |
| Inorganic - Potassium Oxide ($K_2O$) | 1.0 |
| Inorganic - Lithium Oxide ($Li_2O$) | 0.5 |
| Inorganic - Silica (SiO2) | 6.3 |
| Water | 69.6 |

In one example, the inorganics (potassium oxide, lithium oxide, and silica) and a portion of the water are premixed and subsequently added to the water, wetting agent, insolubilizer, and biocide to make the slurry.

In another example, the premix includes Klebofon™1524 and Klebofon™1542 (both of PQ Corporation). Klebofon™1524 is a slurry of approximately 41.5 wt % water, 10.7 wt % $K_2O$, 0.8 wt % $Li_2O$, and 27.0 wt % $SiO_2$. Klebofon™1542 is a slurry of approximately 67.0 wt % water, 2.5 wt % $Li_2O$, and 20.5 wt % $SiO_2$. One example slurry made using a premix of Klebofon™1524 and Klebofon™1542 is shown below:

| Component | Composition (wt %) |
| --- | --- |
| Wetting Agent - Silica Flour ($SiO_2$) | 15.5 |
| Insolubilizer - Zinc Oxide (ZnO) | 6.0 |
| Water | 67.7 |
| Biocide - Silver Oxide (AgO) | 1.1 |
| Klebofon ™ 1524 | 9.25 |
| Klebofon ™ 1542 | 18.45 |

In the above compositions, the wetting agent promotes wetting between condensed water and the hydrophilic coating 34 on the slurper bars 12. As is known, the amount of wetting agent used corresponds to the degree of wetting obtained in the hydrophilic coating 34. The insolubilizer catalyzes polymerization of the lithium silicate, potassium silicate, and silica to form an inorganic matrix. The amount of insolubilizer used corresponds to the degree of polymerization. The biocide inhibits growth of micro-organisms within the heat exchanger 10.

The slurry is applied to the slurper bars 12 using known application methods, such as spraying or dipping, and is cured at an elevated temperature. The above compositions provide enhanced wetability onto the slurper bars 12, improved adhesion to the slurper bars 12 during slurry application, more uniform coating thickness compared to previously known slurries, and a slurry pot life three to four times greater than previously known hydrophilic coating slurries.

The slurry is cured at a temperature of about 500° F. for about four hours. This time and temperature provides the benefit of toughening the cured hydrophilic coating 34 compared to previously known hydrophilic coatings. It is thought that the curing time of four hours, which is considerably longer than conventional curing times, promotes additional polymerization of the lithium oxide during curing to toughen the hydrophilic coating 34. This minimizes cracking and flaking of the cured hydrophilic coating 34.

During curing, the lithium oxide polymerizes with the silica to form a glassy matrix that includes lithium silicate. The glassy matrix includes interstitial sites that hold, for example, the biocide and zinc oxide. If the interstitial sites are large, such as in previously known potassium and borosilicate coatings, the biocide and zinc oxide are permitted to move out of the interstitial sites into condensed water from a passing air stream. The glassy matrix that includes lithium silicate, however, has smaller interstitial sites that retain the biocide and zinc oxide such that they cannot readily move into the condensed water on the slurper bars 12.

The cured hydrophilic coating 34 exhibits a reduced dissolution rate of the silver oxide biocide compared to previously known hydrophilic coatings. In one example, the hydrophilic coating 34 was found to have a silver oxide dissolution rate that was significantly less than currently known hydrophilic coatings. This provides the benefit of holding the silver oxide within the hydrophilic coating 34 rather than the silver oxide dissolving into the condensed water. This reduces weight loss during use and precipitates that form downstream scaling.

The cured hydrophilic coating 34 also provides enhanced wetability for condensed water on the slurper bars 12 and strongly bonds to the slurper bars 12. The enhanced wetability provides the benefit of an increased wicking effect of the condensed water and the strong bond minimizes cracking and flaking.

After curing, the slurper bars 12 and hydrophilic coating 34 are washed with water to remove unreacted slurry components and loose debris. In one example, the pH of effluent wash water is monitored to determine the degree of washing. A pH above about 7.5 indicates that a significant amount of basic components remain in the hydrophilic coating 34. A pH below about 7.5 indicates that most of the basic components have been removed and that no additional washing is needed.

The feature of monitoring the pH provides the benefit of gauging whether or not basic components have been removed from the hydrophilic coating 34. Residual basic components may contribute to cracking, flaking, or degradation of the hydrophilic coating 34 during use. Monitored removal of the basic components minimizes the negative effects of the residual bases.

Although a preferred embodiment of this invention has been disclosed, a worker of ordinary skill in this art would recognize that certain modifications would come within the scope of this invention. For that reason, the following claims should be studied to determine the true scope and content of this invention.

We claim:

1. An antimicrobial hydrophilic coating slurry comprising:
   between about 13.9 wt % and about 17.1 wt % of a wetting agent;
   between about 5.4 wt % and about 6.6 wt % of an insolubilizer;
   between about 1.0 wt % and about 1.2 wt % of a biocide agent;
   between about 6.8 wt % and about 8.8 wt % of an inorganic material comprising lithium oxide, the balance being water.

2. The slurry as recited in claim 1, wherein the slurry includes:
   between about 15.2 wt % and about 15.8 wt % of said wetting agent;
   between about 5.9 wt % and about 6.1 wt % of said insolubilizer;
   about 1.1 wt % of said biocide agent; and
   between about 7.7 wt % and about 7.9 wt % of said inorganic material comprising lithium oxide and the balance being water.

3. The slurry as recited in claim 2, wherein the slurry includes:
   about 15.5 wt % of said wetting agent;
   about 6.0 wt % of said insolubilizer;
   about 1.1 wt % of said biocide agent; and
   about 7.8 wt % of said inorganic material comprising lithium oxide and the balance water.

4. The slurry as recited in claim 1, wherein said inorganic material includes $Li_2O$, $SiO_2$, and $K_2O$.

5. The slurry as recited in claim 4, wherein said inorganic material consists of about 0.5 wt % $Li_2O$, about 6.3 wt % $SiO_2$, and about 1.0 wt % $K_2O$.

6. The slurry as recited in claim 1, wherein the insolubilizer is zinc oxide (ZnO).

7. The slurry as recited in claim 1, wherein the biocide is silver oxide (AgO).

8. The slurry as recited in claim 1, wherein the inorganic material includes $Li_2O$, $SiO_2$, and $K_2O$ in respective wt. % amounts of $X_{Li2O}$, $X_{SiO2}$, and $X_{K2O}$, and $X_{SiO2} > X_{K2O} > X_{Li2O}$.

9. The slurry as recited in claim 8, wherein $X_{K2O} + X_{Li2O} < X_{SiO2}$.

10. The slurry as recited in claim 8, wherein $X_{K2O} + X_{Li2O}$ is greater than the amount of the biocide agent.

11. The slurry as recited in claim 8, wherein the amount of the inorganic material is greater than a combined amount of the insolubilizer and the biocide agent.

* * * * *

UNITED STATES PATENT AND TRADEMARK OFFICE
CERTIFICATE OF CORRECTION

PATENT NO. : 8,124,113 B2
APPLICATION NO. : 11/220159
DATED : February 28, 2012
INVENTOR(S) : Peyton et al.

Page 1 of 1

It is certified that error appears in the above-identified patent and that said Letters Patent is hereby corrected as shown below:

ON THE TITLE PAGE:

Item 75 Inventor John W. Steele's information should read as follows:

--John W. Steele, New Hartford, CT (US)--

Signed and Sealed this
Eighth Day of May, 2012

David J. Kappos
*Director of the United States Patent and Trademark Office*